United States Patent
Doraiswamy et al.

(10) Patent No.: US 12,083,493 B2
(45) Date of Patent: Sep. 10, 2024

(54) SELECTIVE ADSORPTION OF HALOCARBON IMPURITIES CONTAINING CL, BR AND I IN FLUOROCARBONS OR HYDROFLUOROCARBONS USING ADSORBENT SUPPORTED METAL OXIDE

(71) Applicant: American Air Liquide, Inc., Fremont, CA (US)

(72) Inventors: Anup Doraiswamy, Bear, DE (US); Nathan Stafford, Damascus, OR (US)

(73) Assignee: American Air Liquide, Inc., Fremont, CA (US)

(*) Notice: Subject to any disclaimer, the term of this patent is extended or adjusted under 35 U.S.C. 154(b) by 275 days.

(21) Appl. No.: 17/192,421

(22) Filed: Mar. 4, 2021

(65) Prior Publication Data
US 2022/0280908 A1 Sep. 8, 2022

(51) Int. Cl.
*B01J 20/08* (2006.01)
*B01D 3/14* (2006.01)
(Continued)

(52) U.S. Cl.
CPC .............. *B01J 20/08* (2013.01); *B01D 3/143* (2013.01); *B01D 3/36* (2013.01); *B01D 53/04* (2013.01); *B01D 53/82* (2013.01); *B01D 53/96* (2013.01); *B01J 20/3458* (2013.01); *C07C 17/383* (2013.01); *C07C 17/389* (2013.01); *B01D 2253/104* (2013.01); *B01D 2253/1124* (2013.01); *B01D 2253/25* (2013.01); *B01D 2256/26* (2013.01); *B01D 2257/2064* (2013.01);
(Continued)

(58) Field of Classification Search
CPC .... B01J 20/08; B01J 20/3458; B01J 2220/56; B01J 2220/58; C07C 17/389; C07C 17/383; B01D 53/04; B01D 53/82; B01D 53/96; B01D 3/36; B01D 3/143
See application file for complete search history.

(56) References Cited

U.S. PATENT DOCUMENTS 2,879,228 A 3/1959 Holeton et al.
5,449,846 A * 9/1995 Fernandez ............ C07C 17/395
570/177
(Continued)

FOREIGN PATENT DOCUMENTS

CN 101293212 10/2008
EP 0 370 688 11/1989
(Continued)

OTHER PUBLICATIONS

International Search Report and Written Opinion for corresponding PCT/US2022/018712, May 24, 2022.
(Continued)

*Primary Examiner* — Youngsul Jeong
(74) *Attorney, Agent, or Firm* — Yan Jiang

(57) ABSTRACT

Methods for purification of a fluorocarbon or hydrofluorocarbon containing at least one undesired halocarbon impurities comprise flowing the fluorocarbon or hydrofluorocarbon through at least one adsorbent beds to selectively adsorb the at least one undesired halocarbon impurities through physical adsorption and/or chemical adsorption, wherein the at least one adsorbent beds contain a metal oxide supported on an adsorbent in an inert atmosphere.

11 Claims, 2 Drawing Sheets

(51) Int. Cl.
*B01D 3/36* (2006.01)
*B01D 53/04* (2006.01)
*B01D 53/82* (2006.01)
*B01D 53/96* (2006.01)
*B01J 20/34* (2006.01)
*C07C 17/38* (2006.01)
*C07C 17/383* (2006.01)
*C07C 17/389* (2006.01)

(52) U.S. Cl.
CPC ............ *B01D 2257/2066* (2013.01); *B01D 2259/40086* (2013.01); *B01D 2259/4009* (2013.01); *B01J 2220/56* (2013.01); *B01J 2220/58* (2013.01)

(56) References Cited

U.S. PATENT DOCUMENTS

| | | |
|---|---|---|
| 5,545,774 A | 8/1996 | Rao |
| 5,574,192 A | 11/1996 | Vanderpuy et al. |
| 5,852,223 A | 12/1998 | Kohno et al. |
| 6,080,905 A * | 6/2000 | Kaminsky ............ C07C 7/12 585/820 |
| 6,815,568 B2 | 11/2004 | Horiba et al. |
| 2004/0030204 A1 | 2/2004 | Wilmet et al. |
| 2012/0323054 A1 | 12/2012 | Knapp |
| 2015/0126786 A1 | 5/2015 | Sharratt et al. |

FOREIGN PATENT DOCUMENTS

| | | | |
|---|---|---|---|
| EP | 0 508 631 | 10/1992 | |
| GB | 2 295 101 | 5/1996 | |
| JP | 2000 247912 | 9/2000 | |
| JP | 2012 193130 | 10/2012 | |
| JP | 2018 127403 | 8/2018 | |
| KR | 10 0317113 | 1/2002 | |
| WO | WO 2014 150889 | 9/2014 | |
| WO | WO-2014150889 A1 * | 9/2014 | ............ C07B 63/00 |

OTHER PUBLICATIONS

Gabelman, A., Adsorption Basics: Part 1, CEP Magazine, Jul. 2017, American Institute of Chemical Engineers, 48-53.

Gabelman, A., Adsorption Basics: Part 2, CEP Magazine, Aug. 2017, American Institute of Chemical Engineers, 38-45.

* cited by examiner

SELECTIVE ADSORPTION OF HALOCARBON IMPURITIES CONTAINING CL, BR AND I IN FLUOROCARBONS OR HYDROFLUOROCARBONS USING ADSORBENT SUPPORTED METAL OXIDE

TECHNICAL FIELD

The present invention relates to methods of selective adsorption of halocarbon impurities containing Cl, Br and I in fluorocarbons (FCs) or hydrofluorocarbons (HFCs) using an adsorbent supported metal oxide, in particular, to methods to purify the fluorocarbons or hydrofluorocarbons and remove undesired impurities.

BACKGROUND

In chemical industry, standard fluorocarbons (FC's) or hydrofluorocarbons (HFC's) commonly used as refrigerants are produced from fluorination of either halocarbons containing Cl, Br and I or hydrocarbons in the presence of metal or metal oxides supported by porous materials such as silica ($SiO_2$), alumina ($Al_2O_3$) etc. as catalyst at elevated temperatures. This reaction process could lead to many undesirable impurities in products (e.g., halocarbons containing Br or I) either in the form of unreacted raw materials or byproducts. While some of these compounds primarily chlorofluorocarbon (CFC) or hydrochlorofluorocarbon (HCFC) impurities are known to lead the cause for ozone depletion, they may also be toxic and be detrimental to processes when these ultrapure FC or HFC gases are used in semiconductor industry. Here is the reaction: Halocarbons (containing Cl, Br or I)+$F_2$/HF→HFC+Byproducts.

For example, U.S. Pat. No. 5,545,774 issued to V. Rao discloses a production of 1, 1, 1, 3, 3, 3,hexafluoropropane (236fa or the trade name of FE-36) by reacting 1, 1, 1, 3, 3, 3, 3-hexachloropropane with HF in the presence of trivalent chromium compound supported on carbon at temperature around 250 to 400° C. U.S. Pat. No. 5,574,192 issued to VanDerPuy et al. discloses a way to produce 1, 1, 1, 3, 3-pentafluoropropane (245fa or HFC-245fa also under the trade name of Enovate and Genetron) by reacting HCFC compounds such as $CCl_3CH_2CHCl_2$, $CF_3CH_2CHCl_2$, $CFCl_2CH_2CHCl_2$ with HF in the presence of fluorination catalyst such as metal halides.

Usage or presence of these impurities need to be restricted in various concentrations levels ranging from percentage to ppm levels depending on the severity of damage to the above-mentioned causes. However, some of these contaminants could be difficult to separate using more widely used processes such as distillation because of their azeotropic interaction with the main product. Although, different ways to separate critical halocarbon impurities containing Cl, Br and I from some of the HFC molecules, including the molecules covered in this invention, have been disclosed, there has been no one generic process developed for all the above-mentioned impurities that may be adapted to different molecules.

For example, US 2012/0323054 to J. Knapp discloses cis-1, 1, 1, 4, 4, 4-hexafluoro-2-butene separated from a mixture containing one or more chloro fluoro olefins by adding an extractive agent. This solvent changes the relative volatility of cis-compound with respect to chloro olefin making it relatively easier to purify using distillation.

EP 0508631 A1 to P. Clayton discloses a way of production & purification of hydrofluoroalkanes from chloro compounds and halohydrofluoroalkanes by passing the compounds in vapor form through a solution of complex metal hydride combined with alkali hydride.

US 2004/0030204 to Wilmet et al. discloses a more generic hydrofluoroalkanes purification including different ways to remove olefinic impurities including reaction with HF, treatment with $Cl_2$ in the presence of a initiator, adsorption onto solid adsorbent (alumina and silica), distillation and & reactive distillation.

U.S. Pat. No. 6,815,568 to Horiba et al. discloses a process of purifying octafluorocyclobutane by reacting crude containing chloro impurities with a decomposing agent (iron oxide and alkaline earth compound) at elevated temperature followed by adsorption with coal tar, molecular sieve or activated carbon to obtain the product.

U.S. Pat. No. 5,852,223 to Kohno et al. discloses a method to reduce the CFC's in hydrofluoroalkanes by reacting the compound with $H_2$ gas and separating the mixture using distillation.

Number of other patents claim similar methods of purification for different fluorocarbons or hydrofluorocarbons.

A. Gabelman in Adsorption Basics Part 1 and Part 2 (2017 CEP Magazine, American Institute of Chemical Engineers) describes the basic operation, design, and mechanisms of adsorption processes including the regeneration of adsorbent beds. Regeneration of adsorbent beds may be performed by contacting the adsorbent with a gas or liquid that contains little or no adsorbate (impurity), contacting the bed with a solvent that has a higher affinity for the adsorbate, increasing the temperature of the adsorbent, or reducing the pressure. Silica gel and activated alumina ($Al_2O_3$) may be used to dry gases or liquids. Silica gel may be regenerated at 120° C. Zeolite molecular sieves 3A, 4A, 5A, and 13X may be used to remove a variety of impurities including water and may be regenerated at 200-300° C.

Use of adsorbents including alumina, silica etc. to adsorb moisture, acids (HF and HCl) solvent vapors and some other organic contaminants from HFC's is a standard practice in chemical industry. The other important applications involve either alumina or metal oxide/metal on adsorbent for catalytic dehydrohalogenation to produce olefins or decomposition of the exhaust gases to protect the environment similar to the ones mentioned in US 2015/126786A to Sharratt et al. and CN 101293212A to Liu, respectively.

U.S. Pat. No. 2,879,228 to Holeton et al. discloses use of silica gel and alumina to remove partially fluorinated compounds from perfluorinated lubricants in liquid phase. KR 100317113 discloses use of alumina and active carbon columns in series to remove HF and halocarbon contaminants in series from HCl stream. GB 2295101 to Leppard et al. discloses uses chi alumina bed to remove halocarbon contaminants from air stream. Other common applications involve use of adsorbents to remove oil or hydrocarbon contaminants from refrigerants.

Using ultra-high pure gases free of impurities is integral to any processes requiring good quality control. Particularly for fine processes involving fabrication of semiconductor devices where margin of error is severely narrow, maintaining the purity of feed gases is quintessential to get the high throughput. Distillation is the more conventional separation technique employed to achieve this purpose, but this process gets extremely difficult when the volatility of the concerned impurity is close to the matrix compound or if it forms an azeotrope/near azeotrope with the desired product.

Thus, a need remains for methods of producing ultrahigh pure FC or HFC gases free of impurities.

SUMMARY

There is disclosed a process for purification of a fluorocarbon or hydrofluorocarbon containing at least one undesired halocarbon impurities comprising the step of flowing the fluorocarbon or hydrofluorocarbon through at least one adsorbent beds to selectively adsorb the at least one undesired halocarbon impurities through physical adsorption and/or chemical adsorption, wherein the at least one adsorbent beds contain a metal oxide supported on an adsorbent in an inert atmosphere.

There is disclosed a process for purification of a fluorocarbon or hydrofluorocarbon containing at least one undesired halocarbon impurities comprising the steps of flowing the fluorocarbon or hydrofluorocarbon through at least one adsorbent beds to selectively adsorb the at least one undesired halocarbon impurities through physical adsorption and/or chemical adsorption, wherein the at least one adsorbent beds contain a metal oxide supported on an adsorbent in an inert atmosphere, and distilling an outlet stream of the at least one adsorbent beds to obtain a purified fluorocarbon or hydrofluorocarbon.

Either of the disclosed processes may include one or more of the following aspects:
- further comprising the step of distilling an outlet stream of the at least one adsorbent beds to obtain a purified fluorocarbon or hydrofluorocarbon;
- the at least one undesired halocarbon impurities including chlorofluorocarbons (CFC), hydrochlorofluorocarbons (HCFC) and Cl-containing, Br-containing, I-containing, or combinations thereof halides;
- the at least one undesired halocarbon impurities including halocarbons that contain halogens bonded to carbon having less electronegative than fluorine;
- the at least one undesired halocarbon impurities including halocarbons that contain halogens bonded to carbon undergo adsorption having less electronegative than fluorine;
- the at least one undesired halocarbon impurities being halocarbons that contain halogens bonded to carbon having less electronegative than fluorine;
- the at least one undesired halocarbon impurities being halocarbons that contain halogens bonded to carbon undergo adsorption having less electronegative than fluorine;
- the halogens having less electronegative than fluorine being Cl, Br and/or I;
- the at least one undesired halocarbon impurities including halocarbons containing Cl, Br and/or I bonded to carbon;
- the at least one undesired halocarbon impurities including halocarbons containing Cl, Br and/or I bonded to carbon undergo adsorption;
- the at least one undesired halocarbon impurities being halocarbons containing Cl, Br and/or I bonded to carbon;
- the at least one undesired halocarbon impurities being halocarbons containing Cl, Br and/or I bonded to carbon undergo adsorption;
- the at least one undesired halocarbon impurities being Cl-containing, Br-containing, I-containing, or combinations thereof halides;
- the at least one undesired halocarbon impurities being Cl-containing, Br-containing, I-containing, or combinations thereof halocarbons;
- the at least one undesired halocarbon impurities being chlorofluorocarbons (CFC) or hydrochlorofluorocarbons (HCFC);
- the at least one undesired halocarbon impurities being chlorofluorocarbons (CFC) and hydrochlorofluorocarbons (HCFC);
- the at least one undesired halocarbon impurities being chlorofluorocarbons (CFC);
- the at least one undesired halocarbon impurities being chlorofluorocarbons (CFC);
- the at least one undesired halocarbon impurities being 2-chloro-1,1,1-trifluoroethane ($C_2H_2F_3Cl$);
- the at least one undesired halocarbon impurities being 2-chloro-1,1,3-trifluoropropene ($C_3H_2F_3Cl$);
- the at least one undesired halocarbon impurities being 2-chloro-1,1,1,2-tetrafluoropropane ($C_2HF_4Cl$);
- the at least one undesired halocarbon impurities being 2-chloro-1,1,1,3,3-pentafluoro-1-propene ($C_3F_5Cl$);
- the at least one undesired halocarbon impurities being 1,1,2-trichlorotrifluoroethane ($C_2F_3Cl_3$);
- the at least one undesired halocarbon impurities being trichloromonofluoromethane ($CFCl_3$);
- the at least one undesired halocarbon impurities being 2,2-dichloro-1,1,1,-trifluoroethane ($C_2HF_3Cl_2$);
- the at least one undesired halocarbon impurities containing halogens having less electronegative than fluoride, e.g., Cl, Br and I, where Cl, Br and I are represented by "X" in the forms of $C_aH_bF_cX_d$ where a is 1-7, b is 0-13, c is 0-15 and d is 1-16 and $C_oF_pX_q$, where o is 1-7, p is 0-15 and q is 1-16;
- the at least one undesired halocarbon impurities containing halogens having less electronegative than fluoride, e.g., Cl, Br and I, where Cl, Br and I are represented by "X" in the forms of $C_aF_cX_d$ where a is 1-7, c is 0-15 and d is 1-16 and $C_oH_pF_qX_r$ where o is 1-7, p is 0-13, q is 0-15 and r is 1-16;
- the fluorocarbon or hydrofluorocarbon being fluorocarbon and hydrofluorocarbon etching gases;
- the fluorocarbon and hydrofluorocarbon etching gases including but being not limited to including their isomers to $CF_4$, $CHF_3$, $CH_2F_2$, $CH_3F$, $C_2F_6$, $C_2HF_5$, $C_3HF_5$, $C_3H_2F_4$, $C_3H_2F_6$, $C_3F_8$, $C_3F_6$, $C_4F_8$, $C_4F_6$, $C_4H_2F_4$, $C_4H_2F_6$, $C_5F_8$, $C_5HF_7$, $C_6F_6$. Additional examples of fluorocarbon and hydrofluorocarbon gases include but are not limited including their isomers to $C_2H_3F_3$, $C_2H_2F_4$, $C_2H_4F_2$, $C_2H_4F_2$, $C_2H_5F$, $C_3H_3F_5$, $C_4F_{10}$, $C_5F_{12}$, $C_6F_{14}$, and $C_7F_{16}$;
- the fluorocarbon and hydrofluorocarbon etching gas being $C_3H_2F_6$, 1,1,3,3,3-hexafluoropropane, 236fa;
- the fluorocarbon and hydrofluorocarbon etching gas being $C_3H_3F_5$, 1,1,1,3,3-pentafluoropropane, 245fa;
- the inert atmosphere being $N_2$, $H_2$, He, Ar, Xe, or combinations thereof;
- the at least one adsorbent beds being one adsorbent bed;
- the at least one adsorbent beds being two adsorbent beds placed in parallel;
- the at least one adsorbent beds each containing multiple beds in series;
- the at least one adsorbent beds each being one long bed with desired dimensions to purify and control the impurity concentrations in the outgoing product;
- the adsorbent being silica, alumina or molecular sieves;
- the metal oxide being CuO or MgO;
- the metal oxide is being CuO supported by alumina;
- a flow rate of the fluorocarbon or hydrofluorocarbon gas into the adsorbent bed in vapor phase ranging from 0.5 slm to 500 l/min;
- a flow rate of the fluorocarbon or hydrofluorocarbon gas into the adsorbent bed in vapor phase ranging from 1 slm to 150 l/min;
- a flow rate of the fluorocarbon or hydrofluorocarbon liquid into the adsorbent bed in liquid phase ranging from 0.1 kg/hr to 100 kg/hour;

a flow rates for the fluorocarbon or hydrofluorocarbon liquid varying between 0.1 kg/hr and 20 kg/hr;
a temperature of the adsorbent bed ranging from −50° C. to 150° C.;
a temperature of the adsorbent bed ranging from 0° C. to 50° C.;
pressure
a purity of the purified fluorocarbons or hydrofluorocarbons being >99.9%;
a purity of the purified fluorocarbons or hydrofluorocarbons being >99.99%;
a concentration of the halocarbon impurities in a feed of the hydrofluorocarbon or fluorocarbon to be purified being less than 5%;
a concentration of the halocarbon impurities in a feed of the hydrofluorocarbon or fluorocarbon to be purified being less than 1000 ppm;
a concentration of the halocarbon impurities in a feed of the hydrofluorocarbon or fluorocarbon to be purified being less than 500 ppm;
a concentration of the halocarbon impurities in a feed of the hydrofluorocarbon or fluorocarbon to be purified being less than 200 ppm;
a concentration of impurities in the purified fluorocarbon or hydrofluorocarbon being <1000 ppm;
a concentration of impurities in the purified fluorocarbon or hydrofluorocarbon being <100 ppm;
a concentration of impurities in the purified fluorocarbon or hydrofluorocarbon being <10 ppm;
a concentration of impurities in the purified fluorocarbon or hydrofluorocarbon being <5 ppm;
a concentration of impurities in the purified fluorocarbon or hydrofluorocarbon being <1 ppm;
a concentration of impurities in the purified fluorocarbon or hydrofluorocarbon being <0.1 ppm;
further comprising the step of regenerating the adsorbent bed at a temperature ranging from 25° C. to 1000° C. with continuously flowing a purge gas through the adsorbent bed;
further comprising the step of regenerating the adsorbent bed at a temperature ranging from 200° C. to 400° C. with continuously flowing a purge gas through the adsorbent bed;
a pressure of the regeneration process being from 1 torr to 100,000 torr;
the purge gas being selected from $N_2$, $H_2$, He, Ar, Xe, Kr or combinations of $N_2$, $H_2$, He, Ar, Xe and Kr;
the purge gas being $N_2$;
the purge gas being $H_2$;
the purge gas being Ar;
the purge gas being Xe;
the purge gas being Kr;
the purge gas being He;
the purge gas being $H_2$ and $N_2$;
the purge gas being $H_2$ and $N_2$ having a percentage of $H_2$ in $N_2$ between 0-100%;
the purge gas being $H_2$ and $N_2$ having a percentage of $H_2$ in $N_2$ greater than 3%; and
the purge gas being combinations of $N_2$, $H_2$, He, Ar, Xe and Kr.

There is disclosed a system for purification of a fluorocarbon or hydrofluorocarbon containing at least one undesired halocarbon impurities comprising at least one adsorbent beds, containing a metal oxide supported on an adsorbent, in an inert atmosphere, adapted and configured to adsorb the at least one undesired halocarbon impurities through physical adsorption and/or chemical adsorption. The disclosed systems may include one or more of the following aspects:

further comprising at least one distillation columns, adapted and configured to distill an outlet stream of the at least one adsorbent beds to obtain a purified fluorocarbon or hydrofluorocarbon;
the metal oxide being CuO or MgO;
a percentage loading of the metal oxide ranging from 0.1% to 99%;
a percentage loading of the metal oxide ranging from 5% to 50%;
the adsorbents being silica, alumina and molecular sieves;
an operating temperature of the at least one distillation columns varying from −50° C. to 150° C.;
an operating temperature of the at least one distillation columns varying from −20° C. to 100° C.;
the at least one undesired halocarbon impurities including chlorofluorocarbons (CFC), hydrochlorofluorocarbons (HCFC) and Cl-containing, Br-containing, I-containing, or combinations thereof halides;
the at least one undesired halocarbon impurities including halocarbons that contain halogens bonded to carbon having less electronegative than fluorine;
the at least one undesired halocarbon impurities including halocarbons that contain halogens bonded to carbon undergo adsorption having less electronegative than fluorine;
the halogens having less electronegative than fluorine being Cl, Br and/or I;
the at least one undesired halocarbon impurities including halocarbons containing Cl, Br and/or I bonded to carbon;
the at least one undesired halocarbon impurities including halocarbons containing Cl, Br and/or I bonded to carbon undergo adsorption;
the at least one undesired halocarbon impurities being Cl-containing, Br-containing, I-containing, or combinations thereof halides;
the at least one undesired halocarbon impurities being Cl-containing, Br-containing, 1-containing, or combinations thereof halocarbons;
the at least one undesired halocarbon impurities including chlorofluorocarbons (CFC), hydrochlorofluorocarbons (HCFC);
the at least one undesired halocarbon impurities containing halogens having less electronegative than fluoride, e.g., Cl, Br and I, where Cl, Br and I are represented by "X" in the forms of $C_aH_bF_cX_d$ where a is 1-7, b is 0-13, c is 0-15 and d is 1-16 and $C_oF_pX_q$, where o is 1-7, p is 0-15 and q is 1-16;
the at least one undesired halocarbon impurities containing halogens having less electronegative than fluoride, e.g., Cl, Br and I, where Cl, Br and I are represented by "X" in the forms of $C_aF_cX_d$ where a is 1-7, c is 0-15 and d is 1-16 and $C_oH_pF_qX_r$ where o is 1-7, p is 0-13, q is 0-15 and r is 1-16;
the fluorocarbon or hydrofluorocarbon being fluorocarbon and hydrofluorocarbon etching gases;
the fluorocarbon and hydrofluorocarbon etching gases including but being not limited to including their isomers to $CF_4$, $CHF_3$, $CH_2F_2$, $CH_3F$, $C_2F_6$, $C_2HF_5$, $C_3HF_5$, $C_3H_2F_4$, $C_3H_2F_6$, $C_3F_8$, $C_3F_6$, $C_4F_8$, $C_4F_6$, $C_4H_2F_4$, $C_4H_2F_6$, $C_5F_8$, $C_5HF_7$, $C_6F_6$. Additional examples of fluorocarbon and hydrofluorocarbon gases include but are not limited including their isomers to $C_2H_3F_3$, $C_2H_2F_4$, $C_2H_4F_2$, $C_2H_4F_2$, $C_2HSF$, $C_3H_3F_5$, $C_4F_{10}$, $C_5F_{12}$, $C_6F_{14}$, and $C_7F_{16}$;

the fluorocarbon and hydrofluorocarbon etching gas being $C_3H_2F_6$, 1,1,1,3,3,3-hexafluoropropane, 236fa;

the fluorocarbon and hydrofluorocarbon etching gas being $C_3H_3F_5$, 1,1,1,3,3-pentafluoropropane, 245fa;

the at least one adsorbent beds being one adsorbent bed;

the at least one adsorbent beds being two adsorbent beds placed in parallel;

the at least one adsorbent beds each containing multiple beds in series;

the at least one adsorbent beds each being one long bed with desired dimensions to purify and control the impurity concentrations in the outgoing product; and the adsorbent being silica, alumina or molecular sieves.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
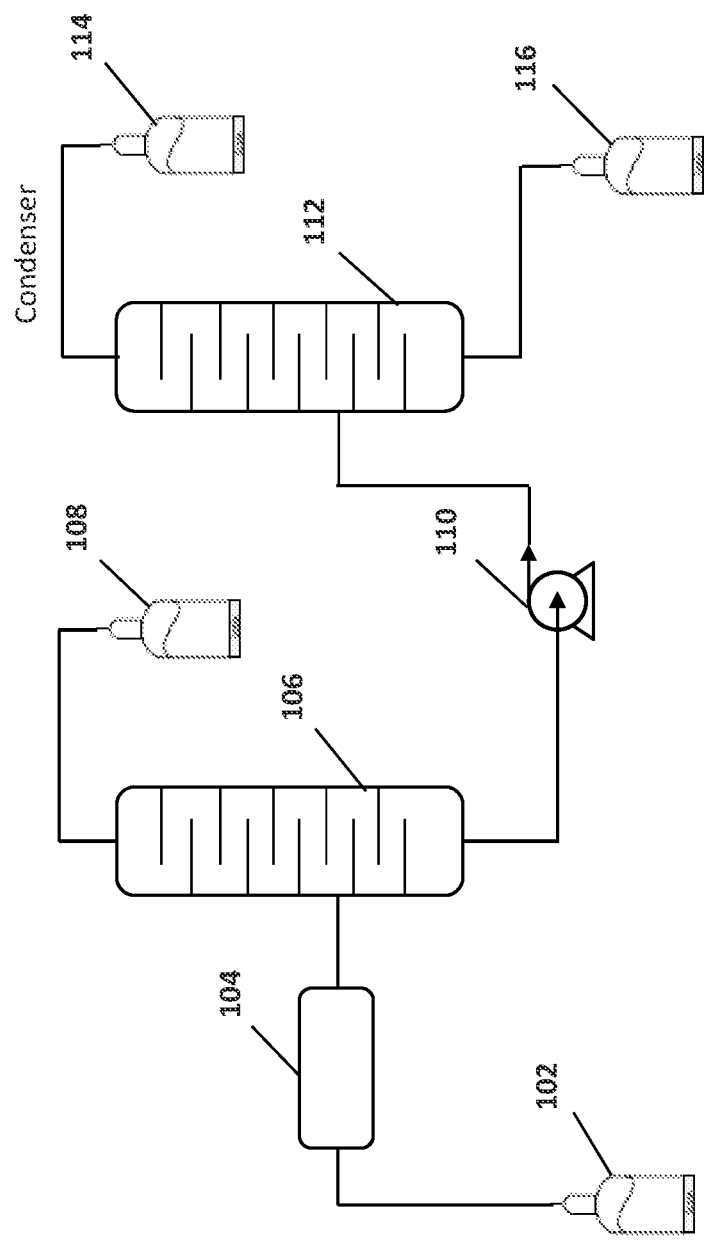
FIG. 1 shows a block diagram of an exemplary embodiment of the disclosed purification systems.

Disclosed are methods of selective adsorption of halocarbon impurities containing Cl, Br and I in fluorocarbons (FCs) or hydrofluorocarbons (HFCs) using an adsorbent supported metal oxide. More specifically, the disclosed methods are the methods for purification of fluorocarbons or hydrofluorocarbons and removal of undesired impurities. The disclosed purification methods remove halocarbon contaminants or impurities containing Cl, Br and/or I, which have less electronegative than fluoride, from the fluorocarbons or hydrofluorocarbons. In one embodiment, the halocarbon contaminants or impurities contained in the fluorocarbons or hydrofluorocarbons may be chlorofluorocarbon (CFC) or hydrochlorofluorocarbon (HCFC). These halocarbons contaminants or impurities are detrimental to applications of the hydrofluorocarbon or fluorocarbon gases, and detrimental to safety and environment as well (e.g., ozone depletion and global warming). These halocarbon contaminants are difficult to remove using distillation with a high yield in a relatively simple unit operation. Some of these impurities may be even difficult to separate from the hydrofluorocarbon or fluorocarbon by conventional distillation. Hence, the disclosed purification methods may be a viable economic alternative by saving on capital costs without compromising on the efficiency of the purification. Highly purified hydrofluorocarbon or fluorocarbons through the disclosed purification methods may have applications in semiconductor industries, metal cleaning processes, and any related areas.

The disclosed method includes flowing a fluorocarbon or hydrofluorocarbon gas that needs to be purified at a particular flow rate through an adsorbent bed that is packed with adsorbent supported metal oxide beads at specified temperature to selectively adsorb undesired impurities through physical adsorption and/or chemical adsorption in an inert atmosphere without any moisture contamination to avoid undesired reactions with the product fluorocarbon. The inert atmosphere may be $N_2$, $H_2$, He, Ar, Xe, or combinations thereof. The usage of hydrogen either in the pure form or in mixture with the other above gases to form the purge gas can be very effective in dehydroxylating and preparation of the bed for adsorption. This step may be followed by distilling an outlet stream of the adsorbent bed to obtain a purified fluorocarbon or hydrofluorocarbon. The distilling step may remove the other impurities unaffected by the adsorption. The purified fluorocarbon or hydrofluorocarbon may be obtained by the flowing step alone or may be obtained by the flowing step and the distilling step. Here the adsorbent bed may include one or more adsorbent beds. For example, the adsorbent bed may be two adsorbent beds placed in parallel. With the disclosed methods, a small amount of desired product might also be adsorbed, which may be later removed during a regeneration process to the adsorbent bed. With the disclosed methods, the critical impurities in the fluorocarbons or hydrofluorocarbons may be removed in an energy efficient manner with a high yield and recovery.

In the disclosed methods, undesired impurities containing halogens Cl, Br and/or I, which have less electronegative than fluorine, bonded to carbon undergo adsorption. The rest of the impurities should be relatively less detrimental to the applications and environment and easy to separate using distillation. Thus, the undesired impurities containing halides or halocarbons (i.e., containing Cl, Br and I) in the fluorocarbons or hydrofluorocarbons may be easily removed without the feed gas reacting with the adsorbent and not compromising on yield.

The purified hydrofluorocarbons have the formula $C_xH_yF_z$ wherein x is 1-7, y is 1-13 and z is 1-16, while the undesired impurities in the feed gas contain halogens having less electronegative than fluoride, e.g., Cl, Br and I, where Cl, Br and I are represented by "X" in the forms of $C_aH_bF_cX_d$, where a is 1-7, b is 0-13, c is 0-15 and d is 1-16 and $C_oF_pX_q$, where o is 1-7, p is 0-15 and q is 1-16.

The purified fluorocarbons have the formula $C_xF_z$ where x is 1-7 and z is 1-16, while the undesired impurities in the feed gas contain halogens having less electronegative than fluoride, e.g., Cl, Br and I, where Cl, Br and I are represented by "X" in the forms of $C_aF_cX_d$ where a is 1-7, c is 0-15 and d is 1-16 and $C_oH_pF_qX_r$ where o is 1-7, p is 0-13, q is 0-15 and r is 1-16.

The undesired halocarbon impurities include Cl-containing, Br-containing, I-containing, or combinations thereof halocarbons, such as, chlorofluorocarbons (CFC) and hydrochlorofluorocarbons (HCFC). The undesired halocarbon impurities include halocarbons that contain halogens bonded to carbon undergo adsorption having less electronegative than fluorine, for example, Cl, Br and/or I. The undesired halocarbon impurities are halocarbons that contain halogens bonded to carbon undergo adsorption having less electronegative than fluorine, for example, Cl, Br and/or I. The undesired halocarbon impurities include halocarbons containing Cl, Br and/or I bonded to carbon undergo adsorption. The undesired halocarbon impurities are halocarbons containing Cl, Br and/or I bonded to carbon undergo adsorption. The undesired halocarbon impurities include Cl-containing, Br-containing, I-containing, or combinations thereof halides. The undesired halocarbon impurities are Cl-containing, Br-containing, I-containing, or combinations thereof halides. The undesired halocarbon impurities include Cl-containing, Br-containing, I-containing, or combinations thereof halocarbons. The undesired halocarbon impurities are Cl-containing, Br-containing, I-containing, or combinations thereof halocarbons. The undesired halocarbon impurities may be chlorofluorocarbons (CFC), hydrochlorofluorocarbons (HCFC), such as 2-chloro-1,1,1-trifluoroethane ($C_2H_2F_3Cl$), 2-chloro-1,1,3-trifluoropropene ($C_3H_2F_3Cl$), 2-chloro-1,1,1,2-tetrafluoropropane ($C_2HF_4Cl$), 2-chloro-1,1,1,3,3-pentafluoro-1-propene ($C_3F_5Cl$), 1,1,2-trichlorotrifluoroethane ($C_2F_3Cl_3$), Trichloromonofluoromethane ($CFCl_3$), and 2,2-dichloro-1,1,1-trifluoroethane ($C_2HF_3Cl_2$).

Fluorocarbon and hydrofluorocarbon gases are traditionally used in a wide variety of applications including as blowing agents to make foams and insulations, fire suppression systems and fire extinguishers, refrigerants, heat transfer mediums, dielectric gases, chemical industrial uses, metal smelting, and the semiconductor industry as plasma etching gases of primarily silicon and silicon containing materials.

Exemplary fluorocarbon and hydrofluorocarbon etching gases that need to be purified may include but are not limited to including their isomers to $CF_4$, $CHF_3$, $CH_2F_2$, $CH_3F$, $C_2F_6$, $C_2HF_5$, $C_3F_5$, $C_3H_2F_4$, $C_3H_2F_6$, $C_4F_6$, $C_3F_6$, $C_4F_8$, $C_4F_6$, $C_4H_2F_4$, $C_4H_2F_6$, $C_5F_8$, $C_5HF_7$, $C_6F_6$. Additional examples of fluorocarbon and hydrofluorocarbon gases include but are not limited including their isomers to $C_2H_3F_3$, $C_2H_2F_4$, $C_2H_4F_2$, $C_2H_4F_2$, $C_2H_5F$, $C_3H_3F_5$, $C_4F_{10}$, $C_5F_{12}$, $C_6F_{14}$, and $C_7F_{16}$.

Here, $C_3H_2F_6$, chemical name 1,1,1,3,3,3-hexafluoropropane, 236fa, is widely used in a variety of applications including a blowing agent and fire suppressing agent. $C_3H_3F_5$, chemical name 1,1,1,3,3-pentafluoropropane, 245fa, is widely used as a blowing agent to create closed cell spray foam insulation.

The to be purified fluorocarbons or hydrofluorocarbons are fed in a form of liquid or gas up to but not limited to 100 kg/hour. However, it is important to note that residence times may vary significantly between a liquid-solid adsorption and a gas-solid adsorption. One of ordinary skilled in the art will understand that a feed rate and phase of the feed may be changed based on the production rate, selectivity of the adsorbent, desired yield, size of the bed and residence times. The residence times in liquid phase higher than that in gas phase may lead to less recovery because of unwanted side reactions between desired hydrofluorocarbons or fluorocarbons and the adsorbent or the metal oxide. The selectivity may be adjusted with the help of the metal oxide, its loading percentage, adsorbent type and the flow rate. If the feed is relatively pure and concentration of impurities in the feed is not that high, a gas feed is preferable to improve the yield and recovery of the primary product.

Instability of fluorocarbons or hydrofluorocarbons with metals and metal oxides is a well-known subject and a common information in the safety data sheet (SDS) of these compounds. Some of the adsorption materials in the disclosed methods are commonly used as catalysts for defluorination of these compounds at elevated temperatures for substitution or elimination reactions. However, when the disclosed adsorption process is performed in a controlled manner at room temperatures with ideal residence times, it may be an effective useful tool to selectively remove the undesired impurities without any by-products.

FIG. 1 shows a block diagram of an exemplary embodiment of the disclosed purification systems in accordance with the present invention. A feed gas with undesired impurities from source cylinder 102 or storage tanks (not shown) is fed to adsorbent bed 104 at desired temperature at a desired flow rate (see below) to optimize adsorption capacity and selectivity. Source cylinder 102 or storage tanks (not shown) may be heated to a desired temperature to reach the desired flow rate. The feed gas may be any fluorocarbon or hydrofluorocarbon gas with halocarbon impurities containing less electronegative halides than fluoride (e.g., Cl, Br and I). Adsorbent bed 104 is packed with adsorbent supported metal oxide beads in an inert atmosphere. Adsorbent bed 104 may be any adsorbent (silica, alumina etc.) supported metal oxide. Preferably, adsorbent bed 104 contains metal oxides, such as CuO, MgO, etc., supported on an adsorbent such as silica, alumina or molecular sieve. In one embodiment, the metal oxide is CuO supported on aluminum. Percentage loading of these metal oxides may vary from 0.1 to 99%. Preferably, the percentage loading of these metal oxides may be from 5% to 50%. The temperature of adsorbent bed 104 may range from −50° C. to 150° C.; preferably, the temperature of adsorbent bed 104 may range from 0° C. to 50° C. The flow rates of the fluorocarbon or hydrofluorocarbon gas may vary from 0.5 slm to 500 l/min. For liquid feeds, the flow rates of the fluorocarbon or hydrofluorocarbon liquid may vary between 0.1 kg/hr and 100 kg/hr. Preferably, the flow rates for the fluorocarbon or hydrofluorocarbon gas may vary from 1 slm to 150 slm and for liquid feeds, the flow rates for the fluorocarbon or hydrofluorocarbon liquid may vary between 0.1 kg/hr and 20 kg/hr. The undesired halocarbon impurities containing chlorine, bromine or iodine may be removed from the feed fluorocarbon or hydrofluorocarbon gas by adsorbent bed 104.

The output or the outlet stream from adsorbent bed 104 contains a product that is a purified fluorocarbon or hydrofluorocarbon and light impurities such as non-condensable gases such as $N_2$ and $CO_2$ and volatile impurities (FC's or HFC's), which have a lower boiling point than the product of the purified fluorocarbon or hydrofluorocarbon, and heavy impurities that have a boiling point higher than that of the product. First distillation column 106 may separate the light impurities from the product and the heavy impurities. The outlet of adsorbent bed 104 may include a particle filtration system (not shown). Particle filters may be composed of but not limited to stainless steel, nickel, Hastelloy or PTFE. The particle filters may remove particles greater than but not limited to approximately 1 nm in size. Commercial filters include for example the Entegris Wafergard or the Pall Corporation Gaskleen line of filters. The output of adsorbent bed 104 is sent to additional purification beds containing either mole sieve or silica to remove moisture followed by first distillation column 106 operated at optimized conditions (see below) to separate the light impurities from the product and the heavy impurities from adsorbent bed 104. The light impurities goes to cylinder 108. The product and heavy impurities are discharged from distillation column 106 and pumped to distillation column 112 by pump 110. One skilled in the art will understand that there are a variety of packing materials used in the distillation columns including but not limited to Heli-Pak, Ceramic Saddles, Raschig Rings, Balls (Teflon or Glass), Wire mesh, and Specialized Structured Packing materials. Afterward, since the boiling point of the product is lower than the heavy impurities, the product comes out of the top of distillation column 112 and collected in cylinder 114 or storage tanks (not shown) and lecture bottles (not shown) through a condenser (not shown) to perform analysis and packaging. The heavy impurities are discharged from the bottom of distillation column 112 and then collected in cylinder 116 or storage tanks (not shown) as a waste. Depending on the impurities contained in the feed fluorocarbons or hydrofluorocarbons, a series of distillation columns may be applied following adsorbent bed 104. It is commonly known in the art of distillation that additional equipment may be used such as additional pumps, flow controllers, valves, pressure transducers, sensors, filters, and the like.

Operating temperature of distillation column 106 and distillation column 112 may vary from −50° C. to 150° C. Preferably, the operating temperature of distillation columns 106 and distillation column 112 may vary from −20° C. to 100° C.

A purity of the product of the purified fluorocarbons or hydrofluorocarbons may be >99.9% by lowering or completely removing undesired impurities through adsorption followed by distillation with the disclosed purification adsorption methods. Preferably, a purity of the product of the purified fluorocarbons or hydrofluorocarbons is >99.99% by lowering or completely removing undesired impurities through adsorption followed by distillation with the disclosed purification adsorption methods.

A concentration of the halocarbon impurities in a feed of the hydrofluorocarbon or fluorocarbon to be purified is less than 5. Preferably, a concentration of undesired Impurities in the feed gas may be <1000 ppm. More preferably, a concentration of undesired impurities in the feed gas may be <500 ppm. Even more preferably, the concentration of undesired impurities in the feed gas may be <200 ppm.

Figure 2:
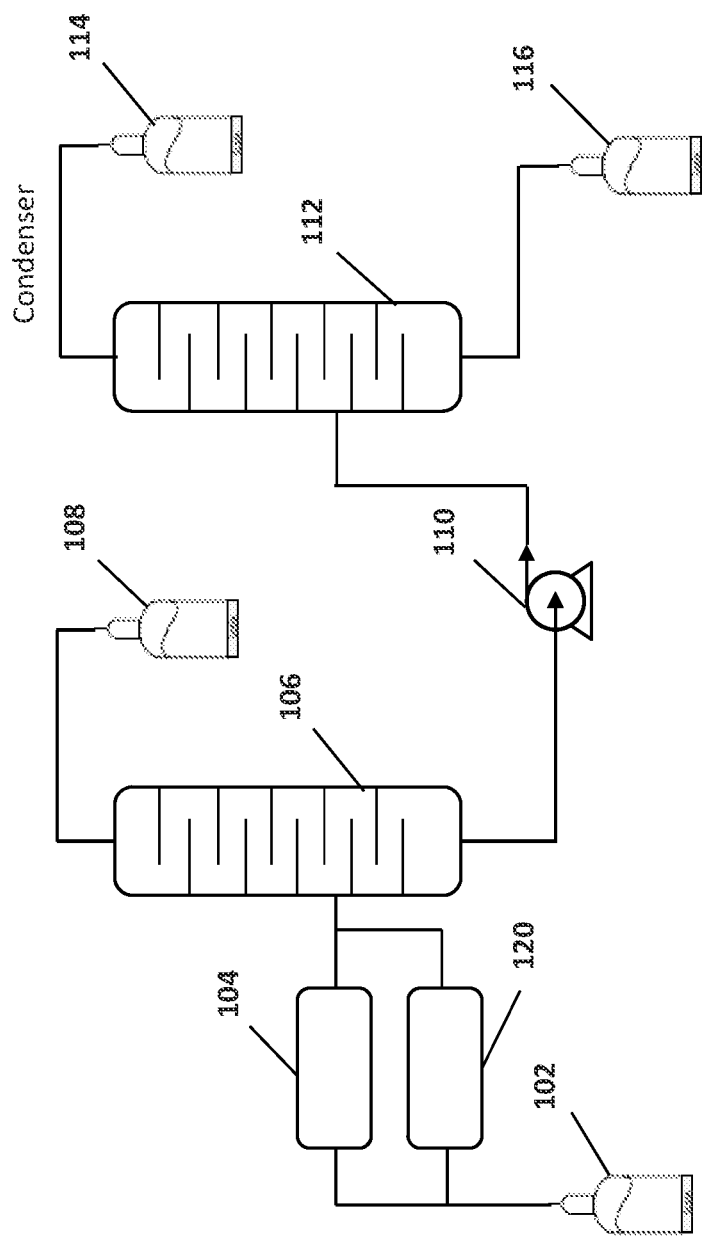
FIG. 2 shows a block diagram of another exemplary embodiment of the disclosed purification systems.

A concentration of undesired impurities in the product of the purified fluorocarbons or hydrofluorocarbons may be <1000 ppm. Preferably, the concentration of undesired Impurities in the product of the purified fluorocarbons or hydrofluorocarbons may be <100 ppm. Preferably, the concentration of undesired Impurities in the product of the purified fluorocarbons or hydrofluorocarbons may be <10 ppm. Preferably, the concentration of undesired Impurities in the product of the purified fluorocarbons or hydrofluorocarbons may be <5 ppm. More preferably, the concentration of undesired Impurities in the product of the purified fluorocarbons or hydrofluorocarbons may be <1 ppm. Even more preferably, the concentration of undesired Impurities in the product of the purified fluorocarbons or hydrofluorocarbons may be <0.1 ppm. The feed gas and product gas and their impurities may be analyzed using a number of analytical instruments including gas chromatograph with detectors such as thermal conductivity detector (TCD), photoionization detector (PID), pulse discharge ionization detector (PDHID), mass spectrometer (MS) and the like. Other detectors could include FTIR, moisture analyzers such as the Meeco Iceman or other analyzers based on $P_2O_5$ technology, as well as Cavity Ring down spectrometer (CRDS). It is understood that each analyzer may detect different impurities and at different detection limits. The analyzers may be used to analyze at points along the exemplary purification system shown in FIG. 1 to include but not limited to source cylinder 102, the outlet of adsorbent bed 104, at various locations on distillation column 106 and 112, cylinder 114 and collection cylinder 116 or storage tanks (not shown), as well as a second adsorbent bed 120 (shown in FIG. 2) in parallel with 104. These analyzers may be used to analyze the gas or liquid streams samples from the process directly or in separate collection vessels. These analyses may be used to change process conditions within the distillation columns or determine breakthrough that has occurred with the adsorbent beds. Breakthrough is defined as the point at which some of the adsorbate begins to pass through the adsorbent bed without being adsorbed.

Adsorbent bed 104 is regenerated at high temperature and continuous purge gas containing $H_2$ in balance inert gas such as He, $N_2$, Ar, Xe, Kr, but more preferably $N_2$. An exemplary continuous purge gas may contain $H_2$ and $N_2$. The term regeneration used here may refer to either a process to prepare adsorbent beds for the first time or a process to remove impurities that have reversibly adsorbed on the adsorbent beds after the adsorbent beds have been used for some time or reached saturation capacity or equilibrium with a feed stream. The temperature of adsorbent bed 104 during regeneration may vary from 25° C. to 1000° C. The adsorbent beds may be regenerated on the system as drawn in FIG. 2 where there are two beds, 104 and 120 in parallel and a switching system that allows you to have one bed in regeneration and one doing the purification. Alternatively, the adsorbent beds after using may be removed to a separate system for regeneration (not shown). Preferably, the temperature of the adsorbent bed during regeneration may vary from 200° C. to 400° C. The regeneration temperature may be chosen based on the specific material in the adsorbent bed and the nature of the adsorbed impurities. The flow of $N_2$ purge during the regeneration is greater than 100 sccm. Preferably, the flow of $N_2$ purge during the regeneration is greater than 500 sccm. It is understood that the gas flow rate during regeneration may vary depending on the size of the adsorbent bed. The pressure of the regeneration process may be from 1 torr to 100,000 torr. One skilled in the art will realize that the pressure of the regeneration process may be chosen based on the specific impurities adsorbed on the adsorbent beds. The purge gas $H_2$ and $N_2$ has a percentage of $H_2$ in $N_2$ between 0-100%. There may be some advantages using <4% $H_2$ in $N_2$ in the regeneration process as concentrations of $H_2$ greater than about 4% in $N_2$ are considered flammable. However, since the flammability limits depend on the inert gas used one skilled in the art may use different concentrations of $H_2$ for the regeneration process.

Depending on the feed gas quality, adsorbent beds 104 and 120 may contain multiple beds in series or one long bed with desired dimensions to purify and control the impurity concentrations in the outgoing product.

EXAMPLES

The following non-limiting examples are provided to further illustrate embodiments of the invention. However, the examples are not intended to be all inclusive and are not intended to limit the scope of the inventions described herein.

Example 1

One adsorbent bed, copper oxide CuO (13%) on alumina from Sigma Aldrich (Part Number: 417971-250G). The other pristine adsorbent bed without the metal oxide loading was activated alumina from Delta adsorbents (Part Number: Activated Alumina AA400G). Physical dimensions of both adsorbents with and without the metal oxide loading are similar (i.e., 14-28 mesh) and both are regenerated under $N_2$ purge at 300° C. prior to the adsorption at a flow rate of 500 sccm for around 5 hours with a residence time of around 46 sec. The hydrofluorocarbon gas $C_3H_2F_6$ (236 fa) which containing CFC impurities including 2-chloro-1, 1,1-trifluoroethane ($C_2H_2F_3Cl$), trichloromonofluoromethane ($CFCl_3$), and 2-chloro-1,1,1,3,3-pentafluoro-1-propene ($C_3F_5Cl_1$) was flowed gas phase through the adsorbent bed at room temperature. After passing through the adsorbent bed loaded with CuO, one of the impurities 2-chloro-1,1,1-trifluoroethane ($C_2H_2F_3C$) in the feed hydrofluorocarbon gas $C_3H_2F_6$ (236 fa) was reduced from ~42 ppm to <1 ppm. While another impurity trichloromonofluoromethane ($CFCl_3$) in the feed fluorocarbon or hydrofluorocarbon gas reduced from ~139 ppm to <1 ppm. Similarly, the other impurity 2-chloro-1,1,1,3,3-pentafluoro-1-propene ($C_3F_5Cl$) reduced from 67 ppm to <1 ppm. When the same feed gas passes through the pristine alumina bed without the metal oxide loading, these impurities, 2-chloro-1,1,1-trifluoroethane ($C_2H_2F_3Cl$), trichloromonofluoromethane ($CFCl_3$), in the feed gas reduced to 23 ppm and 46 ppm respectively. All impurities were measured using gas chromatograph mass spectrometry.

Example 2

The gas $C_3H_3F_5$, 245fa was flowed gas phase through the alumina loaded with CuO adsorbent bed at room temperature. The concentration of one of the impurities 1,1,2-trichlorotrifluoroethane ($C_2F_3Cl_3$) reduces from 284 ppm to <1 ppm while the concentration of 2-chloro-1,1,3-trifluoropropene ($C_3H_2F_3Cl$) reduces from 969 ppm to <1 ppm. Also concentration of 2,2-dichloro-1,1,1-trifluoroethane ($C_2HF_3Cl_2$) impurity reduced from 16 ppm in feed gas to <1 ppm in the product. However, concentration of 2-chloro-1,1,1,2-tetrafluoroethane ($C_2HF_4Cl$) went down from 530 ppm to 45 ppm after single pass through the adsorbent bed containing copper oxide loaded on alumina.

Example 3

The adsorbent bed may be regenerated with pure $N_2$, pure $H_2$ or a mixture of $H_2$ and $N_2$, Studies performed to evaluate and compare the capacities of the adsorbent beds regenerated with pure $N_2$ and 3.5% $H_2$ in $N_2$ balance (flow rate of 1000 sccm at 300° C.) indicated that the adsorption capacity to remove 2-chloro-1,1,1-trifluoroethane ($C_2H_2F_3Cl$) impurity in 236fa increases by >10× (10 times) when the bed is regenerated with $N_2$ and $H_2$ mixture compared to just $N_2$, i.e. for a bed regenerated with just $N_2$, breakthrough point for this impurity in 236fa which is passed through the bed at 100 sccm occurs at 45 min while the adsorbent bed regenerated with 3.5% $H_2$ in $N_2$ balance tested at the same flow rate hits breakthrough after 480 min.

Example 4

During the distillation of 236fa gas at room temperature using a batch distillation column (4' length and 2" diameter) and propak packing, it was observed that some of the chlorine impurities formed azeotropic mixtures with the 236 fa causing difficulties in purification. Especially the two impurities 2-chloro-1,1,1-trifluoroethane ($C_2H_2F_3Cl$) (feed concentration 29 ppm) and 2-chloro-1,1,1,3,3-pentafluoro-1-propene ($C_3F_5Cl$) (feed concentration 47 ppm) did not show much separation across the distillation column and may only be reduced to 27 ppm and 42 ppm respectively.

Example 5

Similar to the above example, when 245 fa gas was purified using the same distillation column, the chlorine impurities 1,1,2-trichlorotrifluoroethane ($C_2F_3Cl_3$) and 2,2-dichloro-1,1,1-trifluoroethane ($C_2HF_3Cl_2$) formed azeotropic mixtures with the 245fa and caused minimal separation. For example, concentration of 1,1,2-trichlorotrifluoroethane ($C_2F_3Cl_3$) reduced from 110 ppm to 60 ppm while 2,2-dichloro-1,1,1-trifluoroethane ($C_2HF_3Cl_2$) reduced only from 6 ppm to 5 ppm respectively after one of the distillation runs at a reboiler temperature of 58° C.

Reference herein to "one embodiment" or "an embodiment" means that a particular feature, structure, or characteristic described in connection with the embodiment may be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used herein, the articles "a" and "an" as used in this application and the appended claims should generally be construed to mean "one or more" unless specified otherwise or clear from context to be directed to a singular form.

As used herein, "about" or "around" or "approximately" in the text or in a claim means ±10% of the value stated.

As used herein, the term "regeneration" may refer to either a process to prepare adsorbent beds for the first time or a process to remove impurities which have reversibly adsorbed on the adsorbent beds after the adsorbent beds have been used for some time or reached saturation capacity or equilibrium with a feed stream.

Standard abbreviations of the elements from the periodic table of elements are used herein. It should be understood that elements may be referred to by these abbreviations (e.g., F refers to fluoride, H refers to hydrogen, C refers to carbon, etc.).

The unique CAS registry numbers (i.e., "CAS") assigned by the Chemical Abstract Service are provided to identify the specific molecules disclosed.

As used herein, the term "hydrocarbon" refers to a saturated or unsaturated function group containing exclusively carbon and hydrogen atoms. As used herein, the term "alkyl group" refers to saturated functional groups containing exclusively carbon and hydrogen atoms. An alkyl group is one type of hydrocarbon. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actors in the absence of express language in the claim to the contrary.

Ranges may be expressed herein as from about one particular value, and/or to about another particular value. When such a range is expressed, it is to be understood that another embodiment is from the one particular value and/or to the other particular value, along with all combinations within said range. Any and all ranges recited herein are inclusive of their endpoints (i.e., x=1 to 4 or x ranges from 1 to 4 includes x=1, x=4, and x=any number in between), irrespective of whether the term "inclusively" is used.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x$ $(NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Although the subject matter described herein may be described in the context of illustrative implementations to process one or more computing application features/operations for a computing application having user-interactive components the subject matter is not limited to these particular embodiments. Rather, the techniques described herein may be applied to any suitable type of user-interactive component execution management methods, systems, platforms, and/or apparatus.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

While embodiments of this invention have been shown and described, modifications thereof may be made by one skilled in the art without departing from the spirit or teaching of this invention. The embodiments described herein are exemplary only and not limiting. Many variations and modifications of the composition and method are possible and within the scope of the invention. Accordingly, the scope of protection is not limited to the embodiments described herein, but is only limited by the claims which follow, the scope of which shall include all equivalents of the subject matter of the claims.

We claim:

1. A process for purification of a fluorocarbon or hydrofluorocarbon containing at least one undesired halocarbon impurities, comprising:
    flowing the fluorocarbon or hydrofluorocarbon through at least one adsorbent beds to selectively adsorb the at least one undesired halocarbon impurities through physical adsorption and/or chemical adsorption, wherein the at least one adsorbent beds contain a metal oxide MgO supported on an adsorbent in an inert atmosphere; and
    regenerating the at least one adsorbent beds after the selective adsorption at a temperature ranging from 500° C. to 1000° C. with continuously flowing a purge gas through the at least one adsorbent beds, wherein the purge gas is either pure $H_2$ or $H_2$ in balance an inert gas selected from He, $N_2$, Ar, Xe or Kr.

2. The process of claim 1, further comprising:
    distilling an outlet stream of the at least one adsorption beds to obtain a purified fluorocarbon or hydrofluorocarbon.

3. The process of claim 1, wherein the at least one undesired halocarbon impurities are Cl-containing, Br-containing, I-containing, or combinations thereof halocarbons.

4. The process of claim 3, wherein the at least one undesired halocarbon impurities are chlorofluorocarbons (CFC) and/or hydrochlorofluorocarbons (HCFC).

5. The process of claim 1, wherein the adsorbent is silica, alumina or molecular sieves.

6. The process of claim 1, wherein a flow rate of the fluorocarbon or hydrofluorocarbon into the at least one adsorbent beds in vapor phase ranges from 0.5 standard liter per minute (SLM) to 500 standard liter per minute (SLM).

7. The process of claim 1, wherein a temperature of the at least one adsorbent beds ranges from −50° C. to 150° C.

8. The process of claim 2, wherein a concentration of impurities in the purified fluorocarbon or hydrofluorocarbon is less than 1000 ppm.

9. A process for purification of a fluorocarbon or hydrofluorocarbon containing at least one undesired halocarbon impurities, comprising:
    flowing the fluorocarbon or hydrofluorocarbon through at least one adsorbent beds to selectively adsorb the at least one undesired halocarbon impurities through physical adsorption and/or chemical adsorption, wherein the at least one adsorbent beds contain a metal oxide MgO supported on an adsorbent in an inert atmosphere;
    regenerating the at least one adsorbent beds after the selective adsorption at a temperature ranging from 500° C. to 1000° C. with a purge gas containing either pure $H_2$ or $H_2$ in balance an inert gas selected from He, $N_2$, Ar, Xe or Kr; and
    distilling an outlet stream of the at least one adsorption beds to obtain a purified fluorocarbon or hydrofluorocarbon.

10. The process of claim 9, wherein a concentration of impurities in the purified fluorocarbon or hydrofluorocarbon is less than 1000 ppm.

11. The process of claim 9, wherein the at least one undesired halocarbon impurities are Cl-containing, Br-containing, I-containing, or combinations thereof halocarbons.

* * * * *